(12) United States Patent
Ishikawa et al.

(10) Patent No.: US 10,082,458 B2
(45) Date of Patent: Sep. 25, 2018

(54) OPTICAL MEASUREMENT DEVICE WITH LIGHT BLOCKING ELEMENT

(71) Applicant: SHIMADZU CORPORATION, Nakagyo-Ku, Kyoto-Shi, Kyoto (JP)

(72) Inventors: Akihiro Ishikawa, Kyoto (JP); Haruhide Udagawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/506,922

(22) PCT Filed: Mar. 5, 2015

(86) PCT No.: PCT/JP2015/056475
§ 371 (c)(1),
(2) Date: Feb. 27, 2017

(87) PCT Pub. No.: WO2016/035361
PCT Pub. Date: Mar. 10, 2016

(65) Prior Publication Data
US 2017/0276602 A1    Sep. 28, 2017

(30) Foreign Application Priority Data

Sep. 1, 2014  (JP) ................................. 2014-176942

(51) Int. Cl.
*G01N 21/359*    (2014.01)
*G01N 21/01*    (2006.01)
(Continued)

(52) U.S. Cl.
CPC ......... *G01N 21/359* (2013.01); *A61B 5/0042* (2013.01); *A61B 5/1455* (2013.01);
(Continued)

(58) Field of Classification Search
CPC ..... G01N 21/359; G01N 21/01; A61B 5/1455
(Continued)

(56) References Cited

U.S. PATENT DOCUMENTS 9,107,583 B2 *  8/2015  Suga ................... G01N 21/474
9,125,552 B2 *  9/2015  Dunki-Jacobs .... A61B 1/00096
(Continued)

FOREIGN PATENT DOCUMENTS

| JP | 2003-227791 | 8/2003 |
| JP | 2004-255075 | 9/2004 |
| JP | 2005-348794 | 12/2005 |

OTHER PUBLICATIONS

PCT/JP2015/056475 International Search Report and Written Opinion dated Jun. 2, 2015, 3 pages—English; 5 pages—Japanese; Certificate of Translation.

*Primary Examiner* — Roy M Punnoose
(74) *Attorney, Agent, or Firm* — Andrew F. Young, Esq.; Lackenbach Siegel, LLP

(57) ABSTRACT

An optical measurement device that comprises an apparatus main element including a light emission aperture, a light emission probe element that includes the optical fibers and that transmits light through it, and the other end of the optical fibers being detachably attached relative to the light emission aperture, and a light block element that blocks the light irradiated from the light emission aperture under the condition in which the light emission probe element connected to the apparatus main element is detached from the light emission aperture.

18 Claims, 9 Drawing Sheets

(51) Int. Cl.
*A61B 5/1455* (2006.01)
*G01N 21/3563* (2014.01)
*G01N 21/63* (2006.01)
*G01N 21/84* (2006.01)
*G02B 23/26* (2006.01)
*A61B 5/00* (2006.01)
*G01N 21/47* (2006.01)

(52) U.S. Cl.
CPC ...... *A61B 5/14552* (2013.01); *A61B 5/14553* (2013.01); *G01N 21/01* (2013.01); *G01N 21/3563* (2013.01); *G01N 21/4795* (2013.01); *G01N 21/63* (2013.01); *G01N 21/84* (2013.01); *G02B 23/26* (2013.01)

(58) Field of Classification Search
USPC .......................................................... 356/445
See application file for complete search history.

(56) References Cited

U.S. PATENT DOCUMENTS

| | | | | |
|---|---|---|---|---|
| 2007/0239232 A1* | 10/2007 | Kurtz | ................... | A61N 5/0613 607/87 |
| 2013/0053703 A1* | 2/2013 | Yamamoto | ........... | A61B 1/0638 600/476 |
| 2013/0211262 A1* | 8/2013 | Suga | ................... | G01N 21/474 600/478 |

* cited by examiner

OPTICAL MEASUREMENT DEVICE WITH LIGHT BLOCKING ELEMENT

CROSS REFERENCE TO RELATED APPLICATIONS

This application relates to and claims priority from Ser. No.: PCT/JP2015/056475 filed Mar. 5, 2015, the entire contents of which are incorporated by reference, which in turn claims priority from JP 2014-176942 filed Sep. 1, 2014.

TECHNICAL FIELD

The present invention relates to an optical measurement device and particularly relates to the optical measurement device comprising a light emission aperture, through which the light is irradiated to a subject.

BACKGROUND

Conventionally, an optical measurement device comprising the light emission aperture, through which the light is irradiated to a subject, is known. Such an optical measurement device is disclosed in Japanese Paten Published: JP2004-255075, for example.

According to the above Patent Document JP2004-255075 A1, the optical measurement device comprises an optical connector that irradiates light to be irradiated to the subject. Such optical measurement device comprises a main element including a laser diode inside thereof, an irradiation probe including an adapter, a detection probe, an optical connector and a connector. And the irradiation probe irradiates the light from the main element to the subject. In addition, the detection probe detects the light reflected (scattered) inside the subject body by the adapter and transmits the detected signal to the maid body. And the detection probe and the main element are attachably and detachably configured through the connector each other, and on the other hand, the irradiation probe and the main body element are connected fixedly through the optical connector.

RELATED PRIOR ART DOCUMENTS

Patent Document

Patent Document 1: Patent Published JP2004-255075

ASPECTS AND SUMMARY OF THE PRESENT INVENTION

Objects to be Solved

However, according to the aspect of the optical measurement device of Patent Document 1 above, the irradiation probe and the main element are fixedly connected through the optical connector each other, so that the irradiation probe and the main element must be moved together with the irradiation probe (without being separated) when the main element is moved (carried). Accordingly, the optical measurement device according to the aspect of Patent Document 1 above has a drawback, i.e., being less portable and inconvenient, relative to the move of the main element. Then, it can be proposed that the main element and the irradiation probe should be configured as attachable-and-detachable relative to the optical connector. However, in such scenario, under the condition in which the irradiation probe is detached from the main element, the light irradiated from the main element may be likely irradiated outside through the optical connector so that the light may be erroneously irradiated to the other object (e.g., human eye) other than the subject per se. Accordingly, it is difficult to prevent such incidental irradiation due to an error, in which the light is irradiated to the other object (e.g., human eye) other than the subject per se from the main element while improving convenience relative to portability of an conventional main element of the apparatus.

The present invention has been proposed in order to solve the aforementioned problems, and an object of the present invention is to provide an optical measurement device that can prevent the light to be irradiated erroneously to the other object other than the subject from the main element of the apparatus.

Means for Solving the Problem

To achieve the above problem, according to the aspect of the present invention, an optical measurement device comprises: a main element (holder) that comprises a light source and a light emission aperture through which the light is irradiated to a subject; an optical transmitting element that comprises an optical fiber and is attachable-and-detachable relative to the light emission aperture and transmits the light to the light emission point arranged to the subject; a light block element that blocks the light irradiated from the light emission aperture to outside under the condition in which the optical transmitting element is detached from the light emission aperture.

According to the aspect of the present invention, as set forth above, the optical measurement device comprises light transmitting element attachable-and-detachable relative to the light emission aperture, so that the move of the main element of the apparatus can be more facilitated, a light block element that blocks the light irradiated outside from the light emission aperture under the condition in which the optical transmitting element is detached from the light emission aperture. a light block element that blocks the light irradiated outside from the light emission aperture under the condition in which the optical transmitting element is detached from the light emission aperture. As results, even when the light is erroneously irradiated from the apparatus main element, it can be prevented that the light would be irradiated to the other object (e.g., human eye) than the subject per se. Accordingly, the incidental irradiation due to an error, in which the light is irradiated to the other object (e.g., human eye) other than the subject per se from the apparatus main element while improving convenience relative to portability of an apparatus main element, can be prevented.

The optical measurement device in accordance with the aspect as described above further preferably comprises the light transmitting element, wherein the light transmitting element can be detached relative to the light emission aperture while the light block element is being installed in the apparatus main element,
and the light block element is in-place on a location of the light axis of the light from the light emission aperture under the condition in which at least the light transmitting element detached from the light emission aperture. In such structure, the light irradiated from the light emission aperture to outside can be blocked by the light block element not only under the condition in which the light transmitting element is detached from the light emission aperture, but also even while the light transmitting element is being attached-and-detached relative to the light emission aperture. Accordingly, the incidental irradiation due to an error, in which the light is irradiated to the other object (e.g., human eye) other than the subject, per se, from the apparatus main element can be prevented.

In such case, preferably, the light block element is installed to the location having a distance away from the light emission aperture as covering the light emission aperture from outside of the apparatus main element, the light transmitting element can be attached and detached relative to the light emission aperture between the light block element and the apparatus main element. In such structure, the light transmitting element can be installed by being inserted into the space between the light block element and the apparatus main element, so that the light block element must not be moved when the light transmitting element is attached and detached. Therefore, even when the light is erroneously irradiated from the apparatus main element, it can be absolutely prevented from that the light would be irradiated to the other object (e.g., human eye) than the subject per se. In addition, the light block element can be exposed outside of the apparatus main element, so that a user can quickly find out a damage or a deformation when e.g., the light block element is damaged or deformed.

The optical measurement device in accordance with the aspect as described above further preferably comprises plural light emission apertures, plural optical fibers, and the light transmitting element, wherein the light transmitting element comprises connection members that include one end of the plural optical fibers that are attached to and detached from the apparatus main element along the light axis direction and the vertical direction, so that the respective plural optical fibers are attached and detached collectively relative to the light emission aperture at one time. Here, the light block element is in-place at the position crossing the light axis to block the light from the light emission aperture. Therefore, if the connection members are installed to the apparatus main element as attachable-and-detachable along the light axis direction, the light block element must be structured as movable or must be installed relatively far away from the apparatus main element. In such scenario, it seems that the structure of the optical measurement device becomes complicated or the optical measurement device per se must be bulky. Then, according to the aspect of the present invention, if the connection members are installed to the apparatus main element along the vertical direction relative to the light axis, the light block element must not be structurally movable and can be in-place relatively close to the apparatus main element, so that it can be avoided that the optical measurement device becomes complicated or bulky. In addition, the connection members attach the plural optical fibers to the plural light emission apertures and detach therefrom at one time, so that the laborious attachment and detachment time can be shortened compared to the time to attach and detach the respective plural optical fibers relative to the individual light emission aperture. Accordingly, the time while the light is leaking outside from the light emission aperture during an attaching and detaching operation of the optical fibers can be shortened, so that the incidental irradiation due to an error, in which the light is irradiated to the other object other than the subject per se from the apparatus main element, can be prevented thereby. In addition, the connection members attach the plural optical fibers to the plural light emission apertures and detaches therefrom at one time, so that the attaching and detaching operation of the optical fibers can be prevented to become complicated.

As results, an operation relative to the move of the apparatus main element (preparation to carry) can be further convenient and improved.

In such case, preferably, the connection members attach and detaches the optical fibers relative to the light emission aperture by being shifted between the light block element and the apparatus main element along the vertical direction to the light axis direction. In accordance with such structure, the user can easily attach and detach the plural optical fibers relative to the plural light emission apertures by only sliding and shifting the connection members between the light block element and the apparatus main element. As results, an operation relative to the shift of the apparatus main element (relative to preparation to carry) can be further convenient and improved because attaching and detaching the light transmitting element are facilitated.

According to the aspect of the optical measurement device in which the above connection members are slided and shifted to attach and detach the optical fibers relative to the light emission aperture, it is preferable that light block element comprises a guide element extending along the parallel direction to the direction of which the connection members are slided and shifted between the light block element and the apparatus main element. Given such structure, the connection members shift along the guide element, so that the connection members can be easily in-place between the light block element and the apparatus main element by sliding and shifting.

According to the optical measurement device that comprises the above connection members, it is preferable that the light block element has an shape capable of covering the connection members along the outer shape thereof. Given such structure, the light block element can be installed close to the connection members as covering the connection members, so that it can be prevented that the structure of the optical measurement device becomes bulky. In addition, it can be prevented that a space between the light block element and the connection members is formed, so that light leak can be prevented when the light is irradiated erroneously in the case of attaching and detaching the connection members relative to the optical measurement device.

The optical measurement device in accordance with the aspect as described above further preferably comprises the light block element that comprises a first surface extending along the light axis installed to the apparatus main element, and a second surface extending from the first surface in the vertical direction to the light axis; and the light transmitting element can be attached and detached inside the space formed between the first surface and the second surface relative to the light emission aperture. In accordance with such structure, the second surface can block the light irradiated from the light emission aperture to outside under the condition, in which the second surface is installed to the apparatus main element, when the light transmitting element is attached and detached relative to the light emission aperture; it can be easily prevented that the light from the apparatus main element is irradiated erroneously to the other object (e.g., human eye) than the subject.

In such case, preferably, the light block element is formed as a shaped box surrounding and enclosing the light emission aperture with the plural first surfaces and the plural second surfaces. Given such structure, the light block element shaped like a box is surrounding and enclosing the light emission aperture with the plural first surfaces and the plural second surfaces, so that the light can be more assuredly prevented from being irradiated erroneously to the object other than the subject in comparison with the case in which the light block element consist of one first surface and one second surface.

In accordance with the light transmitting element in which the above light block element can be attached and detached relative to the light emission aperture, it is preferable that the light block element comprises a shutter element that shifts between the position at which the light irradiated outside from the light emission aperture is blocked and the position at which the light irradiated outside from the light emission aperture is not blocked. Given such structure, the light block element comprising the shutter element can be installed to the light emission aperture of the apparatus main element or inside of the apparatus main element, so that it can be prevented that the structure of the optical measurement device becomes bulky compared to the case in which the light is installed outside the apparatus main element.

Effect of the Invention

Accordingly, the incidental irradiation due to an error, in which the light is irradiated to the other object (e.g., human eye) other than the subject per se from the apparatus main element while improving convenience relative to portability of an apparatus main element, can be prevented.

DETAILED DESCRIPTION OF THE PREFERRED EMBODIMENTS

The inventor sets forth specific Embodiments of the present invention based on the following FIGs.

Embodiment 1

First, referring to FIG. 1 to FIG. 4, the inventor illustrates the system of the optical measurement device 100 according to the aspect of the Embodiment 1 of the present invention.

According to the aspect of the Embodiment 1, the inventor sets forth an optical measurement device 100 designed portable and carryable as an example of the optical measurement device.

Figure 1:
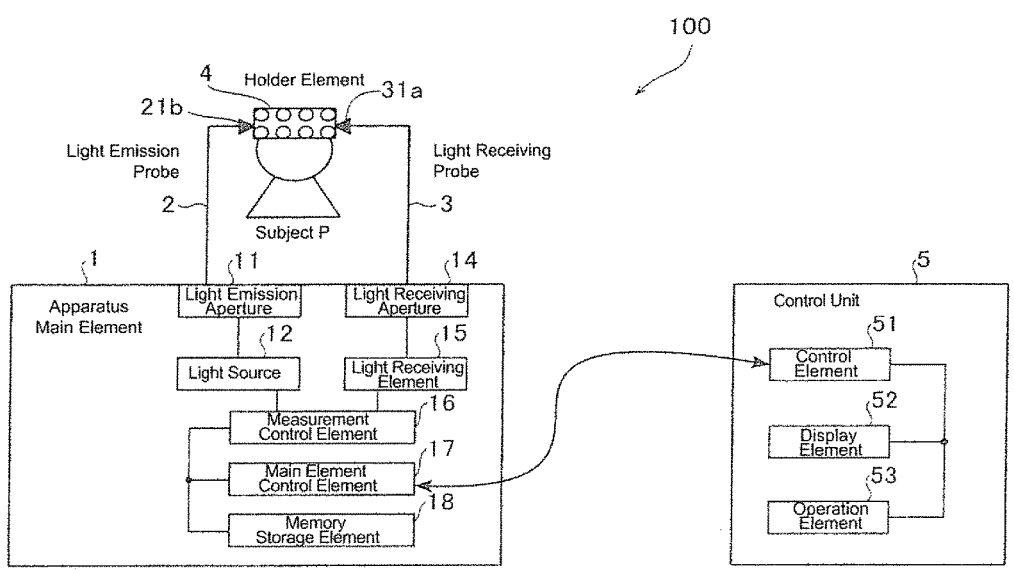
FIG. 1 is a block view illustrating an entire structure of an optical measurement device according to the aspect of the Embodiment 1.

Referring to FIG. 1, an optical measurement device 100, according to the aspect of the present Embodiment, comprises: an apparatus main element 1, a light emission probe element 2, a light receiving probe element 3, a holder element 4 and a control unit 5. In addition, the light emission probe element 2 and the light receiving probe element 3 are installed to the apparatus main element 1, and the light emission probe element 2 and the light receiving probe element 3 are connected to the holder element 4. And the holder element 4 is in-place on the subject P (e.g., on the human head surface). In addition, the light emission probe element 2 is an example of an light transmitting element of the present invention.

Figure 2:
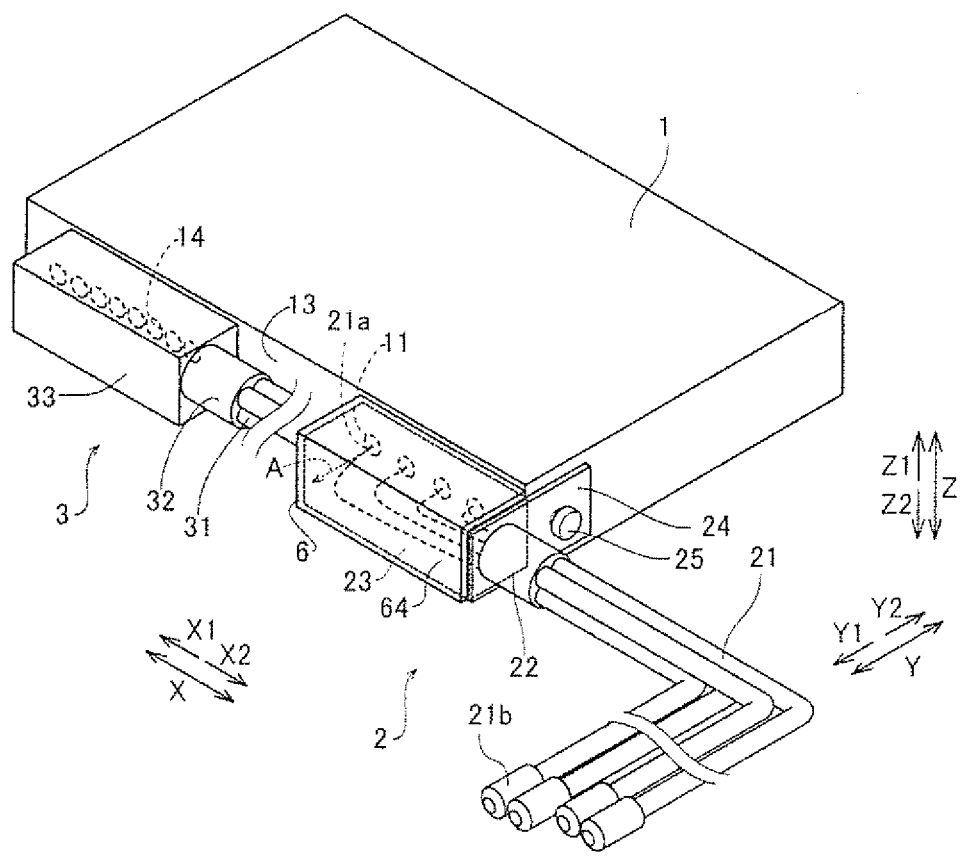
FIG. 2 is a perspective view illustrating an entire structure of an optical measurement device according to the aspect of the Embodiment 1.
Figure 3:
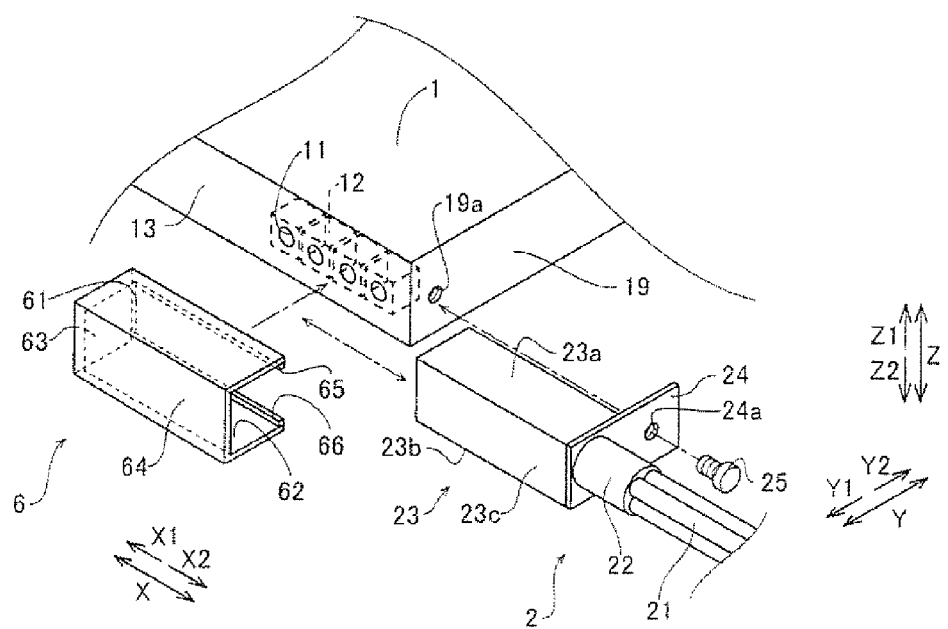
FIG. 3 is an exploded perspective view illustrating attaching and detaching the light emission probe element in FIG. 2.

Referring to FIG. 2, FIG. 3, the apparatus main element 1 comprises the light emission aperture 11 and a light source element 12 (referring to FIG. 3). The light source element 12 can irradiate a measurement light having a near-infrared light wavelength region. The light emission aperture 11 irradiates the light irradiated from the light source element 12 outside the apparatus main element 1 (toward the direction of the light axis A, the arrow Y1 direction side).

Referring to FIG. 2, the apparatus main element 1 is formed as a rectangular parallelepiped. Four light emission apertures 11 are installed to the side surface 13 of the one side of the apparatus main element 1 (side surface in the arrow Y1 direction). the four light emission apertures 11 are in-place in a constant distance each other on the straight line along the X-direction. And referring to FIG. 3, the total of four light source elements 12 are installed inside (side in the arrow Y2 direction) the apparatus main element 1 relative to each light emission aperture H. In addition, the light source element 12 can irradiate the light having e.g., 3 wavelengths 780 nm, 805 nm, and 830 nm, and the light source element 12 comprises laser diodes corresponding to respective 3 wavelengths. Further, referring to FIG. 2, the light source element 12 is not shown.

The light emission probe element 2 comprises 4 optical fibers 21, a band member 22 that bands 4 optical fibers together, a connection member 23 enclosing one end 21a of 4 optical fibers 21, fixing members 24 and a fastener member 25.

Here, according to the aspect of the Embodiment 1, the light emission probe element 2 is attachable-and-detachable relative to the light emission aperture 11. Specifically, the light emission probe element 2 attaches and detaches the connection member 23 of the light emission probe element 2 relative to the light emission aperture 11, so that one end 21a of respective 4 optical fibers 21 can be attached and detached relative to the light emission aperture 11 at one time. Accordingly, one end 21a of respective 4 optical fibers 21 guides the light irradiated from the light emission aperture 11 to the other end 21b of the optical fibers 21 mounted to the holder 4 through the optical fibers 21. In addition, the other end 21b is an example of "light emission aperture" of the present invention.

The light receiving probe element 3 comprises 8 optical fibers 31, a band member 32 that bands 8 optical fibers 31 together, a connection member 33 enclosing one end (not shown in FIG) of 8 optical fibers 31, fixing members 24 and a connection member 33. In addition, the connection member 33 is attachably and detachably connected to the apparatus main element 1 with such as screws (not shown in FIG.) and the respective one ends of 8 optical fibers 31 are attachable-and-detachable relative to the the light receiving aperture 14, set forth later.

Referring to FIG. 1, the holder element 4 is structured as the other end 21b of the optical fibers 21 of the light emission probe element 2 and the other end 31a of the optical fibers 31 of the light emission probe element 3 can be set on the holder element 4. And the optical measurement device 100 irradiates the measurement light from the other end 21b of the optical fibers 21 of the light emission probe element 2 to the subject P. In addition, the measurement light transmitted through the subject P and/or reflected (reflected inside body) therefrom is incident to the other end 31a of the optical fibers 31 of the light receiving probe element 3 in-place on the holder element 4. And the light receiving probe element 3 guides the incident measurement light to the one end of the optical fibers 31.

And referring to FIG. 2, a light receiving aperture 14 is installed to the one side surface 13 of the apparatus main element 1. Eight light receiving apertures 14 are installed to the side surface 13 of the one side of the apparatus main element 1 (side surface in the Y1 direction indicated by the arrow). The eight light receiving apertures 14 are in-place in a constant distance each other along the X-direction. And referring to FIG. 3, the light receiving elements 15 (referring to FIG. 1) are installed inside (in the arrow Y2 direction side) the apparatus main element 1 relative to each light receiving aperture 14. And the light receiving element 15 receives the measurement light set forth above through the one end of the optical fibers 31 and the light receiving apertures 14.

Referring to FIG. 1, the optical measurement device 100 comprises a measurement control element 16. The measurement control element 16 controls the light irradiation of the light source element 12 and acquiring the data relative to the strength of the measurement light from the light receiving element 15.

In addition, the optical measurement device 100 comprises a main element control element 17 and a memory storage element 18. The main element control element 17 controls the memory storage element 18 to store the date relative to the strength of the measurement light from the light receiving element 15. In addition, the main element control element 17 is interactively communicable with a control unit 5 by a wired or wireless connection. And the main element control element 17 transmits the data stored in the memory storage element 18 to the control unit 5 and also acquires the control signals including the operation data from the control unit 5.

In addition, the control unit 5 comprises the control element 51 and a display element 52 and an operation element 53.

Here, a hemoglobin content in the brain increases in the activated region corresponding to the cerebral activity relative to the subject P, so that an absorption amount of the measurement light due to hemoglobin increases. Accordingly, the optical measurement device 100 can acquire variation of the hemoglobin content along with the cerebral activity based on the obtained strength of the measurement light. In addition, the hemoglobins are discriminated between oxy-hemoglobin combined with oxygen and deoxy-hemoglobin not combined with oxygen, which have different light absorption characteristics each other. Therefore, the optical measurement device 100 measures using the measurement light having plural wavelengths (e.g., 780 nm, 805 nm and 830 nm) considering difference between the light absorption characteristics and the control element 51 of the control unit 5 calculates each hemoglobin content and the total content thereof on the basis of strengths of measurement light of each obtained respective wavelengths As results, the optical measurement device 100 can non-invasively acquire a variation of the hemoglobin content along with the cerebral activity on the basis of strength of the incident measurement light to the light receiving probe element 3, i.e., a variation of blood flow content and an activated condition of oxygen metabolism. And the optical measurement device 100 measures the wide cerebral region with a measurement channel at plural points using the plural optical fibers 21 of the light emission probe element 2 and the plural optical fibers 31 of the light receiving probe element 3, so that the optical measurement device 100 can obtain the 2-dimensional distribution relative to which region of the brain is active and how such region functions. And the optical measurement device 100 displays the above 2-dimensional distribution on the display element 52 of the control unit 5.

In addition, the operation element 53 of the control unit 5 can accepts an input input from a user The control element 51 controls a communication in-between the apparatus main element and also, control so as to display the 2-dimensional distribution on the display element 52 based on the input operation by the user.

Here, referring to FIG. 3, according to the aspect of the Embodiment 1, the optical measurement device 100 comprises a light block element 6. The light block element 6 is installed to the side surface 13 of the one side of the apparatus main element 1 (side surface in the Y1 direction indicated by the arrow) with screws and so forth. The light block element 6 comprises a top surface 61 (in the arrow Z1 direction) formed like a plate respectively extending along the light axis A direction (the arrow Y1 direction) from the one side surface 13, the under surface 62 (the arrow Z2 direction) and the side surface 63 (the arrow Z1 direction). In addition, the top surface 61, the under surface 62 and the side surface is an example of a "first surface".

In addition, the light block element 6 comprises the light block surface 64 extending along the vertical direction (X-direction and Z-direction) to the light axis A, which is connected to the side end in each Y1 direction of the top surface 61, the under surface 62 and the side surface 63. The light block surface 64 is made of e.g., a metal plate having light blocking property against the light irradiated from the light emission aperture 11 (light source element 12). In addition, the light block surface 64 is an example of the "second surface" and "guide element" of the present invention.

Referring to FIG. 2, the light block surface 64 is set in-place in the location crossing the light axis A of the light irradiated from the light emission aperture 11 under the condition in which the light block element 6 is installed to the one side surface 13. As results, the light block surface 64 can block the light even when the light is irradiated erroneously outside the apparatus main element 1 from the light emission aperture 11 under the condition (detached condition) in which the light emission probe element 2 (connection member 23) is not mounted to the light emission aperture 11.

In such way, the light block element 6 is installed so as to cover the light emission aperture 11 from the outside of the apparatus main element 1 (from the direction indicated by the arrow Y1). Specifically, the light block element 6 has the top surface 61, the under surface 62, the side surface 63 and the light block surface 64, and thereby has an opening toward the direction indicated by the arrow X2, so that the light block element 6 can be formed like a box enclosing the light emission aperture 11. In addition, the light block element 6 has a shape capable of covering the connection members 23 along the outer shape thereof. Followingly, a preset space into which the connection members 23 are inserted from the direction indicated by the arrow X2 is created inside the light block element 6 between the light block element and the one side surface 13.

Figure 4:
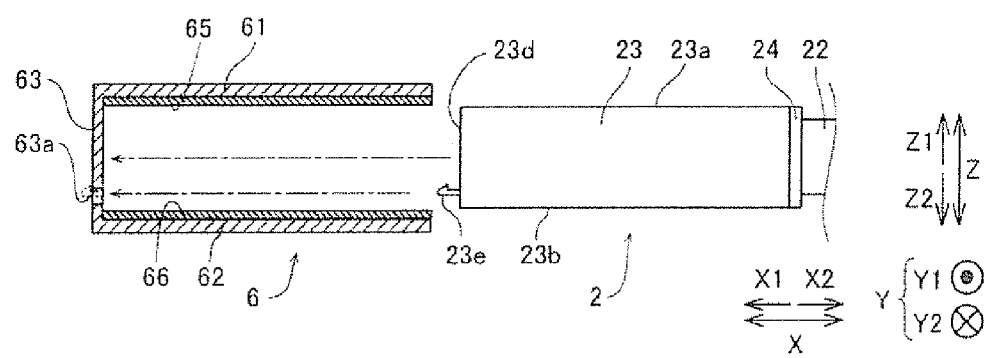
FIG. 4 is a partial schematic cross sectional view illustrating a light block element and the light emission probe element.

Referring to FIG. 3, FIG. 4, according to the aspect of the Embodiment 1, the light emission probe element 2 is attachable-and-detachable relative to the light emission aperture 11 under the condition in which the light block element 6 is installed to the apparatus main element 1. In addition, the light emission probe element 2 is attachable-and-detachable relative to the light emission aperture 11 between the light block element 6 and the apparatus main element 1 (inside the space formed by the top surface 61, the under surface 62, the side surface 63 and the light block surface 64). Specifically, the connection members 23 of the light emission probe element 2 can attach and detach (the one end 21a of) the optical fibers 21 relative to the light emission aperture 11 by being shifted between the light block element 6 and the apparatus main element 1 along the vertical direction (X-direction) to the direction of the light axis A.

Further specifically, the upper guide 65 extending along the X-direction is installed in the light emission aperture 11 side (direction side indicated by the arrow Z2) of the top side 61 of the light block element 6 and in addition, the side of the apparatus main element 1 (direction side indicated by the arrow Y2. In addition, the lower guide 66 extending along the X-direction is installed in the light emission aperture 11 side (the arrow Z1 direction) of the underside 62 of the light block element 6 and in addition, the side of the apparatus main element 1 (direction side indicated by the arrow Y2). And when the connection members 23 are slid and shifted (attached and detached) between the light block element 6 and the apparatus main element 1, the upper guide 65 and the lower guide 66 can respectively contact (be guided by) to the top end surface 23a and the bottom end surface 23b. Further, the upper guide 65 and the lower guide 66 are examples of "guide elements" of the present invention.

In addition, the arrow Y1 direction side of the connection members 23 is guided by the light block surface 64. Specifically, the apparatus main element 1 side of the light block surface 64 and the side end surface 23c of the connection members 23 contact each other when the connection members 23 are slid and shifted in between the light block element 6 and the apparatus main element 1. Accordingly, the light block surface 64 functions even as the guide of the connection members 23. In such way, the light block element 6 and the connection members 23 can slide and shift while contacting each other, so that the one end 21a of the optical fibers 21 inside the connection members 23 can be set more accurately in-place in the location of the light emission aperture 11.

In addition, referring to FIG. 4, a fitting element 23e is mounted to the connection members 23. The fitting element 23d is mounted as projected from the side end surface of the arrow X1 direction side of the connection members 23, so that the fitting element 23e can fit in the opening element 63a installed to the side surface 63 of the light block element 6. Accordingly, once the connection members 23 is installed between the light block element 6 and the apparatus main element 1, the connection members 23 cannot easily (e.g., because of own weight of connection members 23 per se) fall away from the location between the light block element 6 and the apparatus main element 1.

In addition, referring to FIG. 3, a fixing element 24 is mounted to the light emission probe element 2. The fixing element 24 is formed as a flat form spreading on the Y2 plane along the side surface 19 in the arrow Y2 direction side of the apparatus main element 1 and mounted in the arrow X2 direction side of the connection member 23. The opening 24a is installed in the arrow Y2 direction side of the fixing element 24. In addition, a screw hole 19a is installed in the location corresponding to the opening 24a in the side surface 19 of the apparatus main element 1. And the fastening element 25 is mounted to the screw hole 19a passing through the opening 24a, so that the connection member 23 can be fixed to the apparatus main element 1. For example, the fastening member 25 can be a "tuck screw (round head scree)". In addition, the optical fibers 21 and the fastening member 25 are connected to the arrow Y1 direction side of the fixing member 24.

The following effects can be obtained according to the aspect of the Embodiment 1.

According to the aspect of the Embodiment 1, as set forth above, the light emission probe element 2 is attachable-and-detachable relative to the light emission aperture 11, so that the move of the apparatus main element 1 can become more convenient. In addition, the light block element 6 that blocks the light irradiated outside from the light emission aperture, under the condition in which the light emission probe element 2 is detached from the light emission aperture 11, is equipped, so that the light irradiated outside from the light emission aperture can be blocked by the light block element 6 even when the light emission probe element 2 is detached from the light emission aperture 11. As results, even when the light is erroneously irradiated from the apparatus main element 1, it can be prevented that the light would be irradiated to the other object (e.g., human eye) than the subject P per se. Accordingly, the incidental irradiation due to an error, in which the light is irradiated to the other object (e.g., human eye) other than the subject P per se from the apparatus main element 1 while improving convenience relative to portability of an apparatus main element, can be prevented.

According to the aspect of the Embodiment 1, the light emission probe element 2 is attachable-and-detachable relative to the light emission aperture 11 under the condition in which the block element 6 is set in-place in the apparatus main element 1, and the light block element 6 is set in-place on the light axis A of the light from the light emission aperture 11 under the condition in which at least the light emission probe element 2 is detached from the light emission aperture 11. In such structure, the light irradiated from the light emission aperture 11 to outside can be blocked by the light block element 6 not only under the condition in which the light emission probe element 2 is detached from the light emission aperture 11, but also even while the light emission probe element 2 is being attached-and-detached relative to the light emission aperture 11. Accordingly, the incidental irradiation due to an error, in which the light is irradiated to the other object (e.g., human eye) other than the subject per se from the apparatus main element 1 can be prevented.

In addition, according to the aspect of the Embodiment 1, as set forth above, the light block element 6 is set in-place in the location in a distance away from the light emission aperture 11 so as to cover the light emission aperture 11 from outside of the apparatus main element 1, and the light emission probe element 2 is attached and detached relative to the light emission aperture 11 between the light block element 6 and the apparatus main element 1. In such way, the light emission probe element 2 can be mounted by being inserted into the space between the light block element 6 and the apparatus main element 1, so that the light block element 6 must not be moved when the light emission probe element 2 is attached and detached. Therefore, even when the light is erroneously irradiated from the apparatus main element 1, it can be more absolutely prevented from that the light would be irradiated to the other object (e.g., human eye) than the subject P per se. In addition, the light block element 6 can be exposed outside the apparatus main element 1, so that a user can quickly find out a damage or a deformation when e.g., the light block element 6 is damaged or deformed.

In addition, according to the aspect of the Embodiment 1, as set forth above, the plural light emission apertures 11 are installed to the optical measurement device 100 and also the plural optical fibers 21 are installed. In addition, the connection members 23, comprising the one end 21a of the plural optical fibers 21, are attached to and detached from the apparatus main element 1 along the light axis direction and the vertical direction (X-direction), so that the respective plural optical fibers 21 are attached and detached collectively relative to the plural light emission apertures at one time. Here, the light block element 6 (light block surface 64) is set in-place at the location crossing the light axis A to block the light from the light emission aperture 11. Therefore, if the connection members 23 are mounted to the apparatus main element 1 along the light axis A direction, the light block element 6 must be structured as movable or must be installed in a distance relatively far away from the apparatus main element 1. In such scenario, it seems that the structure of the optical measurement device 100 becomes complicated or the optical measurement device 100 per se must be bulky. Then, according to the aspect of the Embodiment 1, the connection members 23 are installed to the apparatus main element 1 along the vertical direction relative to the light axis A direction (X-direction), the light block element 6 must not be structurally movable and can be set in-place relatively close to the apparatus main element 1, so that it can be avoided that the optical measurement device 100 becomes complicated or bulky.

In addition, the connection members 23 attach the plural optical fibers 21 to the plural light emission apertures 11 and detach therefrom at one time, so that the laborious attachment and detachment time for attaching and detaching the optical fibers 21 can be shortened compared to the time to attach and detach the respective plural optical fibers 21 relative to the individual light emission aperture 11. Accordingly, the time while the light is leaking outside from the light emission aperture 11 during an attaching and detaching operation of the optical fibers 21 can be shorten, so that the incidental irradiation due to an error, in which the light is irradiated to the other object other than the subject P per se from the apparatus main element 1, can be prevented thereby. In addition, the connection members 23 attaches the plural optical fibers 21 to the plural light emission apertures 11 and detaches therefrom at one time, so that the attaching and detaching operation of the optical fibers 21 can be prevented to become complicated. As results, an operation relative to the move of the apparatus main element 1 (preparation to carry) can be further convenient and improved.

In addition, according to the aspect of the Embodiment 1, as set forth above, the connection members 23 attaches and detaches the optical fibers 21 relative to the light emission aperture 11 by being shifted between the light block element 6 and the apparatus main element 1 along the vertical direction (X-direction) to the light axis A direction. In such way, the user can easily attach and detach the plural optical fibers 21 relative to the plural light emission apertures 11 by only sliding and shifting the connection members 23 between the light block element 6 and the apparatus main element 1. As results, an operation relative to the shift of the apparatus main element 1 (relative to preparation to carry) can be further convenient and improved because attaching and detaching the light emission probe element 2 are facilitated.

In addition, according to the aspect of the Embodiment 1, as set forth above, the light block element 6 comprises the upper guide 65 and the lower guide 66 extending along the parallel direction (X-direction) to the direction in which the connection member 23 slides and shifts between the light block element 6 and the apparatus main element 1. Given such structure, the connection member 23 shifts along the upper guide 65 and the lower guide 66, so that the connection member 23 can be easily set in-place between the light block element 6 and the apparatus main element 1 by sliding and shifting.

Further, according to the aspect of the Embodiment 1, as set forth above, the light block element 6 has an shape capable of covering the connection member 23 along the outer shape thereof. Given such structure, the light block element can be installed close to the connection member 23 as covering the connection member 23, so that it can be prevented that the structure of the optical measurement device 100 becomes bulky. In addition, it can be prevented that a space between the light block element 6 and the connection members is formed, so that light leak can be prevented when the light is irradiated erroneously in the case of attaching and detaching the connection member 23 relative to the optical measurement device 100.

Further, according to the aspect of the Embodiment 1, as set forth above, the light block element 6 comprises the top surface 61, the under surface 62 and the side surface 63 along the light axis A direction, which are mounted to the apparatus main element 1, and the light block surface 64 extending along the vertical direction (XZ plane) from the top surface 61 to the light axis A, the under surface 62 and the side surface 63. Further, the light emission probe element 2 is attachable-and-detachable relative to the light emission aperture 11 in the space formed with the top surface 61, the under surface 62 and the side surface 63 and the light block surface 64. In accordance with such structure, the light block surface 64 can block the light irradiated outside from the light emission aperture 11 under the condition, in which the light block surface 64 is installed to the apparatus main element 1, when the light transmitting element is attached and detached relative to the light emission aperture 11; it can be easily prevented that the light is irradiated erroneously from the apparatus main element 1 to the other object (e.g., human eye) than the subject P per se.

Further, according to the aspect of the Embodiment 1, as set forth above, the light block element 6 is formed like a box with the top surface 61, the under surface 62, the side surface 63 and the light block surface 64, so that the light block element 6 can enclose and cover the light emission aperture 11. Given such structure, the light block element 6 has a box form with the top surface 61, the under surface 62, the side surface 63 and the light block surface 64 and encloses and covers the light emission aperture 11, so that the light can be more assuredly prevented from being irradiated erroneously from the apparatus main element 1 to the object other than the subject P in comparison with the case in which the light block element 6 is formed with the top surface 61 and the light block surface 64.

Embodiment 2

Figure 5:
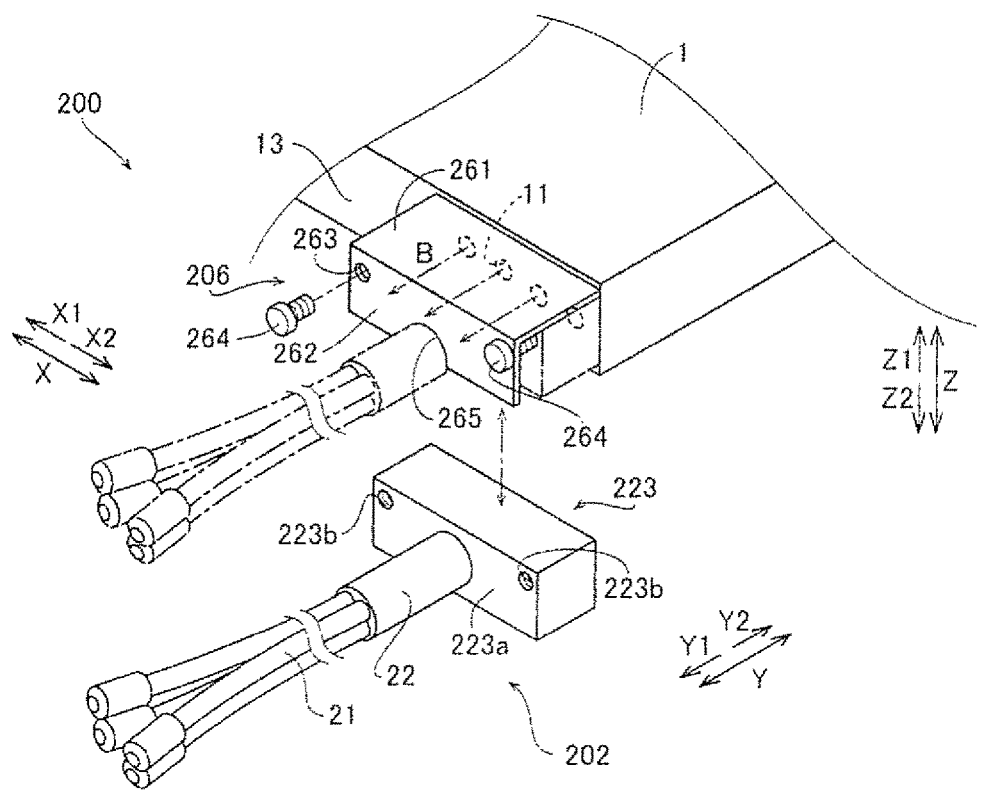
FIG. 5 is an exploded perspective view illustrating the light block element and the light emission probe element of the optical measurement device according to the aspect of the Embodiment 2.

Next, referring to FIG. 5, the inventor sets forth a structure of an optical measurement device 200 according to the aspect of the Embodiment 2 An optical measurement device 200, according to the aspect of the Embodiment 2, comprises a light block element having a top surface and a light block surface but not having an under surface and a side surface, and such aspect is different from the optical measurement device, according to the aspect of the Embodiment 1, comprising the light block element having the top surface, the under surface, the side surface and the light block surface. Further, the same element as illustrated according to the aspect of the Embodiment 1 is not set forth while providing the identical reference sign according to the aspect of the Embodiment 2.

Referring to FIG. 5, an optical measurement device 200, according to the aspect of the Embodiment 2, comprises: a light emission probe element 202 having optical fibers 21, the fixing member 22 and a connection member 223.

The connection member 223 comprises one end of the optical fibers 21 inside thereof as well as the connection member 23 according to the aspect of the Embodiment 1. The connection member 223 connects to the optical fibers 21 (and fixing member 22) in the middle of the side surface 223a of the arrow Y1 direction side. And the connection members 223 can attach and detach the optical fibers 21 relative to the light emission aperture 11 by being slid and shifted between the light block element 206 and the apparatus main element 1 along the vertical direction (Z-direction).

Further, each screw hole 223b is installed near the end of the side surface 223a of the connection member 223 in the arrow X1 direction and the arrow X2 direction.

Here, according to the aspect of the Embodiment 2, the light block element 206 comprises the top surface 261 along the light axis B direction, which is mounted to the apparatus main element 1, and the light block surface 262 extending along the vertical direction (XZ plane) from the end of the arrow Y1 direction side of the top surface 261 to the light axis B.

The light block surface 262 that blocks the light irradiated (light axis B direction) from the light emission aperture 11 to outside under the condition in which the light emission probe element 202 (connection member 223) is detached from the light emission aperture 11. The light block surface 262 comprises an opening 263 and a screw 264 passes through the opening 263 toward the arrow Y2 direction and screwed together with the screw hole 223b, so that the light emission probe element 202 (connection member 223) can be fixed between the light block element 206 and the apparatus main element 1.

Further, the light block surface 262 comprises a cut 265. The cut 265 is formed as a corresponding shape (arc shape) to the upper part of the fixing member 22. The 265 disposes the upper part of the optical fibers 21 (and fixing member 22) inside and allows the optical fibers 21 to run away. In addition, the cut 265 is set in-place in the light axis B direction, at which the light emission aperture 11 cannot overlap. Accordingly, while the light block element 206 is blocking the light (of the light axis B) irradiated outside from the light emission aperture 11, the light block element can prevent the optical fibers 21 to bend in the arrow Z2 direction under the condition in which the connection member 223 is being mounted.

Further, other elements of the optical measurement device 200 according to the aspect of the Embodiment 2 are the same as the optical measurement device 100 according to the aspect of the Embodiment 1.

The following effects can be obtained according to the aspect of the Embodiment 2.

Further, according to the aspect of the Embodiment 2, as set forth above, the light block element 206 comprises the top surface 261 along the light axis B direction (arrow Y1 direction), which is mounted to the apparatus main element 1, and the light block surface 262 extending along the vertical direction (arrow Z2 direction) to the light axis B from the top surface 261. Accordingly, differently from the light block element 6 according to the aspect of the Embodiment 1, the light block element 206 does not comprise an under surface 62 and a side surface 63 and so forth, so the complex aspect thereof can be avoided.

Further, other effects of the optical measurement device 200 according to the aspect of the Embodiment 2 are the same as the optical measurement device 100 according to the aspect of the Embodiment 1.

Embodiment 3

Figure 6:
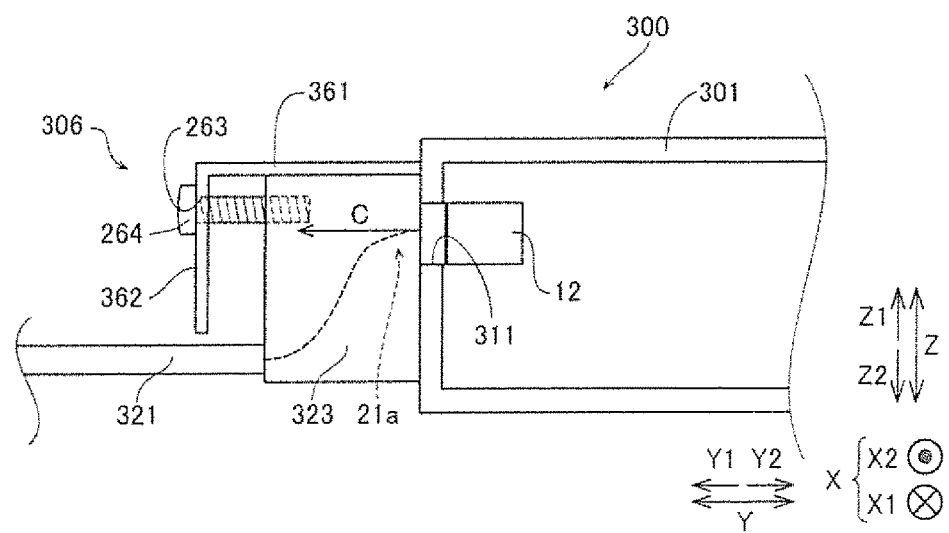
FIG. 6 is a schematic side view illustrating the optical measurement device according to the aspect of the Embodiment 3.
Figure 7:
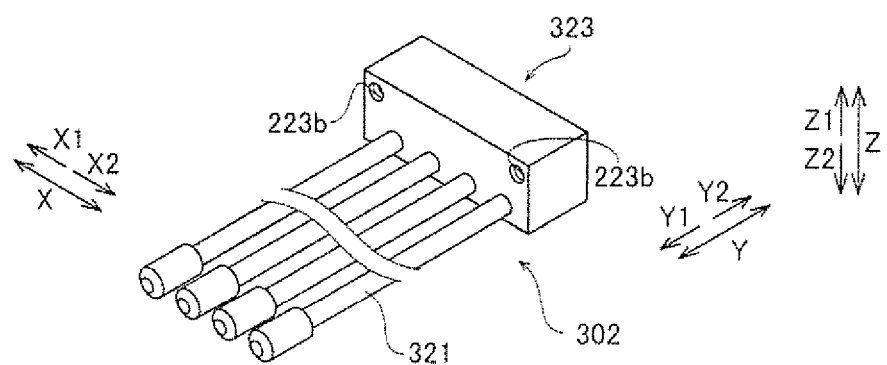
FIG. 7 is a perspective view illustrating the light emission probe element according to the aspect of the Embodiment 3.

Next, referring to FIG. 6 and FIG. 7, the inventor sets forth an aspect of the optical measurement device 300 according to the aspect of the Embodiment 3. Differently from the optical measurement device, according to the aspect of the Embodiment 2, comprising the light block element having a cut, the optical measurement device 300 according to the aspect of the Embodiment 3 comprises light block element having no cut. Further, the same element as illustrated according to the aspect of the Embodiment 1 and the Embodiment 2 is not set forth while providing the identical reference sign according to the aspect of the Embodiment 3.

Referring to FIG. 6 and FIG. 7, an optical measurement device 300, according to the aspect of the Embodiment 3, comprises: a light emission probe element 302 having 4 optical fibers 321 and a connection member 323.

Here, according to the aspect of the Embodiment 3, 4 optical fibers 321 are connected individually to the connection member 323 in a constant distance away each other in the X-direction. In addition, each optical fiber 321 is in-place in the Z2 direction side of the surface of the arrow Y1 direction of the connection member 323. Specifically, under the condition in which the connection member 323 is mounted to the light emission aperture 311, the location at which the optical fiber 321 is connected is set in the X2 direction side rather than the location at which the light emission aperture 311 is in-place.

The light block element 306 comprises; the top surface 361 along the light axis C direction (arrow Y1 direction), which is mounted to the apparatus main element 301, and the light block surface 362 extending along the vertical direction (arrow Z2 direction) to the light axis C from the end in the Y1 direction of the top surface 361.

The light block surface 362 does not comprise a cut 265 differently from the light block surface 262 according to the aspect of the Embodiment 2. On the other hand, the end side of the Z2 direction side of the light block surface 362 is in-place in the arrow Z2 direction side rather than the light emission aperture 311 and the arrow Z1 direction side rather than the optical fiber 321 (connection location of the optical fiber 321 to the connection member 323). Accordingly, the light block element 306 can block the light even when the light is irradiated toward the light axis B direction from the light emission aperture 311 under the condition in which the connection member 323 is detached from the light emission aperture 311.

Further, other elements of the optical measurement device 300 according to the aspect of the Embodiment 3 are the same as the optical measurement device 100 (optical measurement device 200) according to the aspect of the Embodiment 1 (Embodiment 2).

The following effects can be obtained according to the aspect of the Embodiment 3.

As set forth above, according to the aspect of the Embodiment 3, 4 optical fibers 321 can be connected individually in a constant distance away each other along the X-direction at the location of the arrow Z2 direction in the surface of the Y1 direction side of the connection member 323. And under the condition in which the connection member 323 is mounted to the light emission aperture 311 and viewing from the arrow Y1 direction side, the location at which the optical fiber 321 is connected is in-place in the Z2 direction side rather than the location at which the light emission aperture 311 is in-place. Accordingly, the light block element 306 can block the light that is irradiated toward the light axis C direction from the light emission aperture 311 under the condition in which the connection member 323 is detached from the light emission aperture 311 without installing the cut 265 as installed for the light block element 206 according to the aspect of the Embodiment 2.

Further, other effects of the optical measurement device 300 according to the aspect of the Embodiment 3 are the same as the optical measurement device 100 according to the aspect of the Embodiment 1.

Embodiment 4

Figure 8:
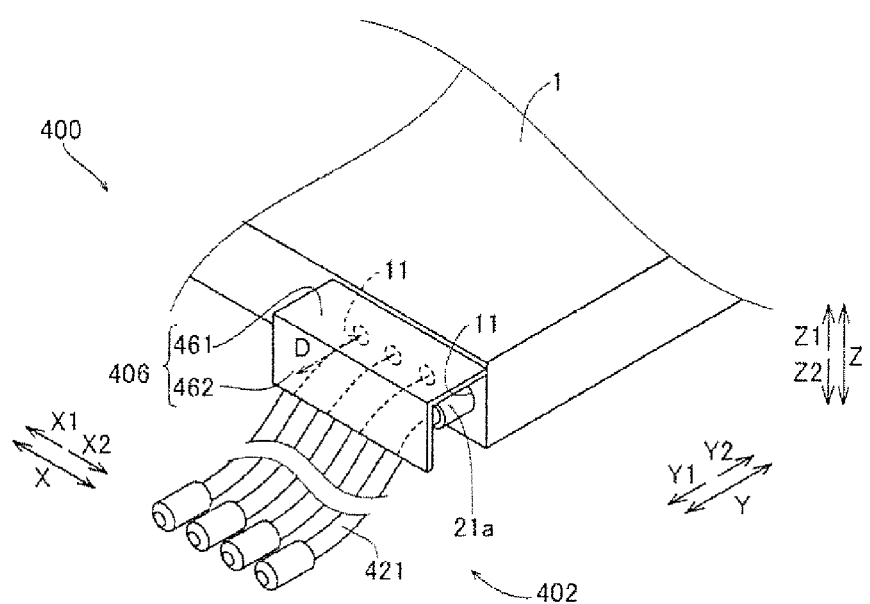
FIG. 8 is a perspective view illustrating the light block element and the light emission probe element of the optical measurement device according to the aspect of the Embodiment 4.

Next, referring to FIG. 8, the inventor sets forth a structure of an optical measurement device 400 according to the aspect of the Embodiment 4. According to the aspect of the Embodiment 4, an optical measurement device 400 does not comprises a connection member, but optical fibers are attachable-and-detachable relative to a light emission aperture based on a connection member in which the one end of the optical fibers are in-place inside differently from the optical measurement device according to the aspect of the Embodiment 1, in which the optical fibers are attachable-and-detachable relative to the light emission aperture. Further, the same element as illustrated in Embodiment 4 is not described in detail while providing the identical reference sign.

Referring to FIG. 8, an optical measurement device 400, according to the aspect of the Embodiment 4, comprises: a light emission probe element 402 having plural (4) optical fibers 421.

Here, according to the aspect of the Embodiment 4, 4 optical fibers 421 are respectively attachable-and-detachable relative to the light emission aperture 11. In addition, the light block element 406 comprising the top surface 461 and the light block element 462 can block the light even when the light is irradiated toward the light axis D direction from the light emission aperture 11 under the condition in which the optical fibers 421 are detached from the light emission aperture 11.

Further, other elements of the optical measurement device 400 according to the aspect of the Embodiment 4 are the same as the optical measurement device 100 according to the aspect of the Embodiment 1.

The following effects can be obtained according to the aspect of the Embodiment 4.

According to the aspect of the Embodiment 4, 4 optical fibers 421 are respectively attachable-and-detachable relative to the light emission aperture 11. Further, the light block element 406 comprises a top surface 461 and a light block surface 462 and blocks the light irradiated from the light emission aperture 11 under the condition in which the optical fibers 421 are detached from the light emission aperture 11 to the light axis D direction. Accordingly, the connection members are not required to be installed, so that the structure of the light emission probe element 402 can be less complicated because the connection members are no longer mandatory.

Further, other effects of the optical measurement device 400 according to the aspect of the Embodiment 4 are the same as the optical measurement device 100 according to the aspect of the Embodiment 1.

In addition, the aspects of the Embodiments disclosed at this time are examples and not limited thereto in any points. The scope of the present invention is specified in the claims but not in the above description of the aspect of the Embodiments and all alternative (alternative examples) are included in the scope of the claims and equivalents thereof.

For example, according to the aspect of the present Embodiments 1 to Embodiment 4 described above, the example of the optical measurement device is portable and carryable, but the present invention is not limited thereto. According to the present invention, the optical measurement device can be a standalone type or can be movable as a cart with wheels.

Figure 9:
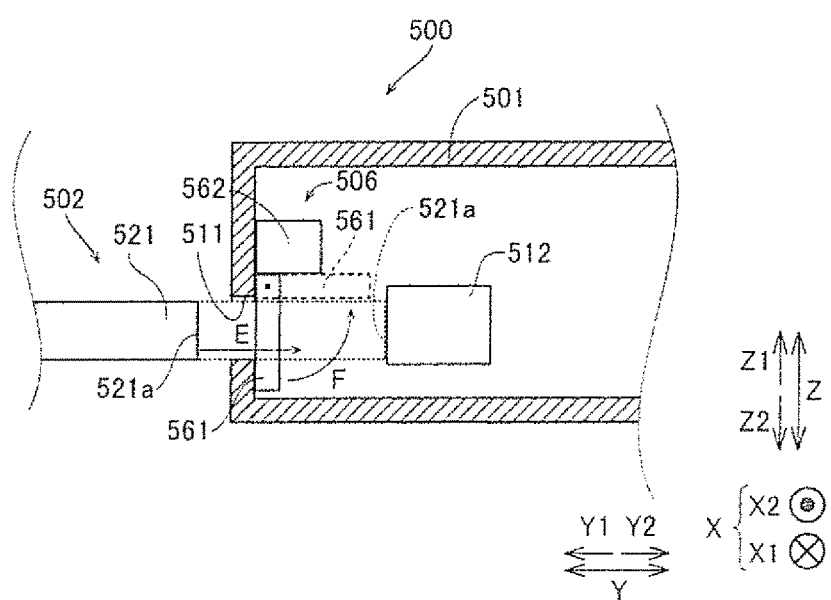
FIG. 9 is a cross sectional view illustrating the structure of the light block element according to the aspect of the Embodiment 1 and the aspect of the alternative Embodiment 1.

In addition, according to the aspect of the Embodiment 1 to Embodiment 4, the light block element of the present invention is installed as covering the light emission aperture from outside of the apparatus main element, so that the aspect, by which th the light irradiated from the light emission aperture 11 to outside area is blocked, is illustrated as Embodiments, but the present invention is not limited thereto. The light block element of the present invention may be installed as covering the light emission aperture from other than the outside of the apparatus main element so that the light irradiated from the light emission aperture to outside can be blocked. Referring to FIG. 9, e.g., according to the aspect of the alternative Embodiment, the light block element 506 installed inside the apparatus main element 501 may block the light irradiated from the light emission aperture 511 (light source 512) to outside.

Here, referring to FIG. 9, according to the aspect of the alternative Embodiment, the optical measurement device 500 comprises an apparatus main element 501, a light emission probe element 502 and a light block element 506. The apparatus main element 501 comprised the light emission aperture 511 and the light source 512, and the light block element 506 is in-place inside the apparatus main element 501. The light block element 506 comprise a shutter element 561 and a bias member 562. The shutter element 561 is set in-place in the location (indicated by the solid line in FIG. 9) blocking the light irradiated from the light source 512 to outside (arrow T1 direction) by that the shutter element 561 is biased by the bias member 562 under the condition in which the light emission probe element 502 (one end of the optical fibers 521a) is not mounted to the light emission aperture 511 (refer to the part indicated by the solid line in FIG. 9). In addition, the shutter element 561 can be shifted to the location, at which the light is not blocked, by that the one end 512a of the optical fiber 521 travels to the arrow E direction and the shutter element 561 is lifted up to the arrow F direction (refer to the part indicated by the dashed line in FIG. 9) under the condition in which the light emission probe element 502 (one end 521a of the optical fiber 521) is mounted to the light emission aperture 511, so that the one end 521a of the optical fiber 521 and the light source 512 can be connected each other.

The light block element 506, according to the alternative Embodiment as set forth above, includes the shutter element 561 that shifts between the location at which the light irradiated from the light emission aperture 11 to outside is blocked (refer to the part indicated by the solid line in FIG. 9) and the location at which the light irradiated from the light emission aperture 11 to outside is not blocked (refer to the part indicated by the dashed line in FIG. 9 under the condition in which the shutter element 561 in FIG. 9 is lifted up to the arrow F direction). Given such structure, the light block element 506 comprising the shutter element 561 can be installed inside the apparatus main element 501, so that it can be prevented that the structure of the optical measurement device 500 becomes bulky compared to the case in which the light block element 506 is installed outside the apparatus main element 501.

In addition, according to the aspect of the Embodiments 1 the Embodiment 4 described above, the example of that 4 light emission apertures of the present invention are installed to the apparatus main element, but the present invention is not limited thereto. According to the aspect of the present invention, other than 4 of such light emission apertures may be installed in the apparatus main element. For example, not more than 3 of such light emission apertures may be installed or at least 5 thereof in the apparatus main element may be installed.

For example, according to the aspect of the present Embodiment 1 to Embodiment 4 described above, 4 of the optical fibers are installed to the light emission probe element 2 and 8 of the optical fibers are installed to the light receiving element, but the present invention is not limited thereto. According to the aspect of the present invention, other than 4 of the optical fibers may be installed to the light emission probe element and other than 8 of the optical fibers may be installed to the light receiving element. For example, 8 (by branching the 4 optical fibers to 8 at the end) of the optical fibers may be installed to the light emission probe element and more than 8 or less than 8 thereof may be installed to the light receiving element.

In addition, according to the aspect of the Embodiment 1 to Embodiment 4, the light block element of the present invention comprises the flat top surface along the direction of the light axis mounted to the apparatus main element and a flat light block surface extending from the top surface along the vertical direction to the light axis, and the light block element can be block the light irradiated from the light emission aperture to outside, but the present invention is not limited thereto. According to the aspect of the present invention, the top surface of the light block element and the light block surface thereof may be not flat, and the light block element blocks the light irradiated from the light emission aperture to outside. For example, the light block surface has a curved surface from the apparatus main element 1 and may block the light irradiated from the light emission aperture to outside.

REFERENCE OF SIGNS

1, 301, 501 Apparatus main element
2, 202, 302, 402, 502 Light emission probe element (light transmittance element)
6, 206, 306, 406, 506 Light block element
11, 311, 511 Light block element
12, 512 Light source element (Light source)
21, 321, 421, 521 Optical fibers
21a, 521a One end (One end of the optical fiber)
21b Other end (light emission point)
23, 223, 323 Connection member
61, 261, 361, 461 Surface (first surface)
62 Under surface (first surface)
63 Side surface (first surface)
64, 262, 362, 462 Light block element (second surface, guide element)
65 Upper guide (guide element)
66 Lower guide (guide element)
100, 200, 300, 400, 500 Optical measurement device
561 Shutter element

What is claimed is:

1. An optical measurement device, comprising:
   a light source;
   an apparatus main body that comprises the light source and a light emission aperture that irradiates a light to a subject;
   a light transmittance element that comprises an optical fiber is detachably attached relative to said light emission aperture and transmits the light to a light sending point arranged relative to said subject;
   a light block element that blocks the light irradiated from said light emission aperture under a condition in which the light transmittance element is detached from said light emission aperture; and
   said light block element is at a location external from said light emission aperature and is covering said light emission aperture from the outside of the apparatus main element;
   said light transmitting element is between said light block element and said apparatus main element in a direction of a light emission from the light emission aperture, and said light transmission element is detachably attached relative to said light emission aperture.

2. The optical measurement device, according to claim 1, wherein:
   said light transmitting element is detachably attached relative to said light emission aperture under the condition in which said light block element is installed to said apparatus main element; and
   said light block element is in-place on a location on a light axis of a light from said light emission aperture under the condition in which at least said light transmitting element detached from said light emission aperture.

3. The optical measurement device, according to claim 1, further comprising :
   a plurality of light emission apertures are installed, and a plurality of optical fibers are installed; and
   said light transmitting element further comprises:
      a plurality of connection members that respectively include one end of said plurality of optical fibers that is detachably attached relative to said apparatus main element along a vertical direction to the direction of said light axis from said light emission aperture, so that the respective plurality of optical fibers are attached and detached collectively relative to the light emission aperture at one time.

4. The optical measurement device, according to claim 3, wherein:
   said connection members attach and detach respective said optical fibers relative to said light emission aperture by being slid and shifted between said light block element and said apparatus main element along the vertical direction to said light axis direction.

5. The optical measurement device, according to claim 4, wherein:
   said light block element further comprises:

a guide element extending along a parallel direction to the direction in which said connection members are slid and shifted between said light block element and said apparatus main element.

6. The optical measurement device, according to claim 3, wherein:
said light block element is shaped to cover said connection members along an outer shape of said connection member.

7. The optical measurement device, according to claim 1, wherein:
said light block element further comprises:
a first surface extending along a direction of a light axis from said light emission aperture installed to said apparatus main element, and a second surface extending from said first surface in a vertical direction to said light axis; and
said light transmitting element is detachably attached relative to a space formed between said first surface and a second surface relative to said light emission aperture.

8. The optical measurement device, according to claim 7, wherein:
said light block element is formed as a box shape surrounding and covering said light emission aperture with a plurality of said first surfaces and a plurality of said second surfaces.

9. An optical measurement device, comprising:
a light source;
an apparatus main body that comprises the light source and a light emission aperture that irradiates a light to a subject;
a light transmittance element that comprises an optical fiber and is detachably attached relative to said light emission aperture and transmits the light to a light sending point arranged relative to said subject;
a light block element is an external cover at a location external from said light emission aperture and blocks light irradiated from said light emission aperture under a condition in which the light transmittance element is detached from said light emission aperture;
wherein said light block element is installed as covering the light emission aperture and blocking the light from an outside of said apparatus main element; and
said light block element further comprises:
a first surface extending along a direction of a light axis from said light emission aperture installed to said apparatus main element, and a second surface extending from said first surface in a vertical direction to said light axis; and
said light transmitting element is detachably attached inside a space formed between said first surface and a second surface relative to said light emission aperture.

10. The optical measurement device, according to claim 9, wherein:
said light block element is formed as a box shape surrounding and covering said light emission aperture with a plurality of said first surfaces and a plurality of said second surfaces.

11. The optical measurement device, according to claim 9, wherein:
said light transmitting element is detachably attached relative to said light emission aperture under the condition in which said light block element is installed to said apparatus main element; and
said light block element is in-place on a location on a light axis of a light from said light emission aperture under the condition in which at least said light transmitting element detached from said light emission aperture.

12. The optical measurement device, according to claim 9, wherein:
a shutter element shifts between a location at which said light irradiated from said light emission aperture to said outside is blocked and a location at which the light irradiated from said light emission aperture to said outside is not blocked.

13. The optical measurement device, according to claim 9, wherein:
said light block element is installed at a location a distance away from said light emission aperture and is covering said light emission aperture from the outside of the apparatus main element, and said light transmitting element is detachably attached relative to said light emission aperture between said light block element and said apparatus main element.

14. An optical measurement device, comprising:
a light source;
an apparatus main body that comprises the light source and a light emission aperture that irradiates a light to a subject;
a light transmittance element that comprises an optical fiber and is detachably attached relative to said light emission aperture and transmits the light to a light sending point arranged relative to said subject;
a light block element that blocks the light irradiated from said light emission aperture under a condition in which the light transmittance element is detached from said light emission aperture;
wherein said light block element is installed as covering the light emission aperture and blocking the light from an outside of said apparatus main element;
a plurality of light emission apertures are installed, and a plurality of optical fibers are installed; and
said light transmitting element further comprises:
a plurality of connection members that respectively include one end of said plurality of optical fibers that are detachably attached relative to said apparatus main element along a vertical direction to the direction of said light axis from said light emission aperture, so that the respective plurality of optical fibers are detachably attached collectively relative to the light emission aperture at one time; and
wherein said light block element has an profile boundary that covers said connection members along an outer shape of said connection member.

15. The optical measurement device, according to claim 14, wherein:
said light transmitting element is detachably attached relative to said light emission aperture under the condition in which said light block element is installed to said apparatus main element; and
said light block element is in-place on a location on a light axis of a light from said light emission aperture under the condition at least said light transmitting element is detached from said light emission aperture.

16. The optical measurement device, according to claim 14, wherein:
said light block element is installed at a location a distance spaced from said light emission aperture and is covering said light emission aperture from the outside of the apparatus main element, and said light transmitting element is detachably attached relative to said light emission aperture between said light block element and said apparatus main element.

17. The optical measurement device, according to claim 14, wherein:
   a shutter element shifts between a location at which said light irradiated from said light emission aperture to said outside is blocked and a location at which the light irradiated from said light emission aperture to said outside is not blocked.

18. The optical measurement device, according to claim 14, wherein:
   said connection members detachably attach respective said optical fibers relative to said light emission aperture by being slid and shifted between said light block element and said apparatus main element along the vertical direction to said light axis direction.

* * * * *